(12) United States Patent
von Büdingen et al.

(10) Patent No.: US 6,569,431 B2
(45) Date of Patent: May 27, 2003

(54) RECOMBINANT ANTIBODY FRAGMENTS AS AUTOANTIBODY ANTAGONISTS

(75) Inventors: Hans-Christian von Büdingen, San Francisco, CA (US); Claude P. Genain, Mill Valley, CA (US); Stephen L. Hauser, Ross, CA (US)

(73) Assignee: The Regents of the University of California, Oakland, CA (US)

( * ) Notice: Subject to any disclaimer, the term of this patent is extended or adjusted under 35 U.S.C. 154(b) by 14 days.

(21) Appl. No.: 09/899,896

(22) Filed: Jul. 5, 2001

(65) Prior Publication Data

US 2002/0072588 A1 Jun. 13, 2002

Related U.S. Application Data

(63) Continuation of application No. 09/691,654, filed on Oct. 17, 2000, now abandoned.
(51) Int. Cl.[7] ..................... A61K 39/395; C07K 16/28
(52) U.S. Cl. ................ 424/142.1; 424/130.1; 424/133.1; 424/137.1; 424/141.1; 424/143.1; 424/152.1; 424/172.1; 530/387.1; 530/387.3; 530/387.5; 530/388.1; 530/388.15; 530/388.2; 530/388.22

(58) Field of Search .............. 530/387.1, 387.33, 530/387.5, 388.1, 388.15, 388.2, 388.22; 424/130.1, 133.1, 137.1, 141.1, 142.1, 143.1, 152.1, 172.1

(56) References Cited

PUBLICATIONS

Bendig "Methods: A Companion to Methods in Enzymology" 1995; 8:83–93.*

\* cited by examiner

Primary Examiner—Phillip Gambel
Assistant Examiner—Jessica H. Roark
(74) Attorney, Agent, or Firm—Richard Aron Osman

(57) ABSTRACT

The invention provides methods and compositions for inhibiting autoantibody binding in demyelinating disease such as multiple sclerosis. The compositions comprise immunoglobulin CDR3 sequences derived from combinatorial phage display libraries selected for high-affinity binding to myelin oligodendrocyte glycoprotein.

15 Claims, No Drawings

SEQUENCE LISTING

```
<160> NUMBER OF SEQ ID NOS: 12

<210> SEQ ID NO 1
<211> LENGTH: 108
<212> TYPE: PRT
<213> ORGANISM: human

<400> SEQUENCE: 1

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
            20                  25                  30

Ala Ile Ser Trp Ala Arg Gln Pro Pro Gly Gln Gly Leu Glu Trp Met
        35                  40                  45

Gly Ala Phe Asp Pro Glu Tyr Gly Ser Thr Thr Tyr Ala Gln Lys Phe
    50                  55                  60

Gln Gly Arg Val Thr Met Thr Ala Asp Thr Ser Thr Ser Thr Ala Tyr
65                  70                  75                  80

Met Glu Leu Ser Ser Leu Arg Pro Glu Asp Thr Ala Val Tyr Tyr Cys
                85                  90                  95

Ala Arg Asp Val Asn Phe Gly Asn Tyr Phe Asp Tyr
            100                 105

<210> SEQ ID NO 2
<211> LENGTH: 100
<212> TYPE: PRT
<213> ORGANISM: human

<400> SEQUENCE: 2

Glu Leu Val Met Thr Gln Ser Pro Ala Thr Leu Ser Leu Ser Pro Gly
 1               5                  10                  15

Glu Arg Ala Thr Val Ser Cys Arg Ala Gly Gln Ser Val Ser Tyr Tyr
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Arg Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Ser Ser Trp Pro Pro
```

-continued

```
                85                  90                  95

Thr Phe Gly Gln
            100

<210> SEQ ID NO 3
<211> LENGTH: 108
<212> TYPE: PRT
<213> ORGANISM: human

<400> SEQUENCE: 3

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
             20                  25                  30

Ala Ile Ser Trp Val Arg Gln Pro Gly Gln Gly Leu Glu Trp Met
         35                  40                  45

Gly Gly Val Asp Pro Glu Tyr Gly Gly Thr Thr Tyr Thr Gln Lys Phe
 50                  55                  60

Gln Gly Arg Val Thr Met Thr Thr Asp Thr Ser Thr Ser Thr Ala Tyr
 65                  70                  75                  80

Met Glu Leu Ser Ser Leu Arg Pro Glu Asp Thr Ala Val Tyr Tyr Cys
                 85                  90                  95

Ala Arg Asp Arg Gly Met Gly Asn Tyr Phe Asp Tyr
            100                 105

<210> SEQ ID NO 4
<211> LENGTH: 100
<212> TYPE: PRT
<213> ORGANISM: human

<400> SEQUENCE: 4

Glu Leu Val Met Thr Gln Ser Pro Ala Thr Leu Ser Leu Ser Pro Lys
  1               5                  10                  15

Glu Thr Ala Thr Leu Ser Cys Arg Ala Ser Gln Ser Val Ser Ser Tyr
             20                  25                  30

Leu Ala Trp Tyr Gln Gln Lys Pro Gly Gln Ala Pro Arg Leu Leu Ile
         35                  40                  45

Tyr Gly Ala Ser Thr Arg Ala Thr Gly Ile Pro Ala Arg Phe Ser Gly
 50                  55                  60

Ser Gly Ser Gly Thr Asp Phe Thr Leu Thr Ile Ser Arg Leu Glu Pro
 65                  70                  75                  80

Glu Asp Phe Ala Val Tyr Tyr Cys Gln Gln Tyr Ser Ser Trp Pro Leu
                 85                  90                  95

Thr Phe Gly Gln
            100

<210> SEQ ID NO 5
<211> LENGTH: 110
<212> TYPE: PRT
<213> ORGANISM: human

<400> SEQUENCE: 5

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
             20                  25                  30

Gly Met Gln Trp Val Arg Gln Ala Pro Glu Gln Gly Leu Glu Trp Met
         35                  40                  45
```

Gly Trp Ile Asn Thr Asn Thr Gly Gly Thr Ser Tyr Ala Gln Lys Phe
            50                  55                  60

Gln Gly Arg Val Thr Met Thr Arg Asp Ala Ser Thr Ser Thr Ala Tyr
 65                  70                  75                  80

Met Glu Leu Ser Ser Leu Arg Pro Glu Asp Thr Ala Val Tyr Tyr Cys
                 85                  90                  95

Ala Arg Asp Ala Thr Arg Ile Leu Ala Asp Val Leu Asp Tyr
            100                 105                 110

<210> SEQ ID NO 6
<211> LENGTH: 99
<212> TYPE: PRT
<213> ORGANISM: human

<400> SEQUENCE: 6

Glu Leu Thr Leu Thr Gln Ser Pro Val Thr Leu Ser Leu Ser Pro Lys
 1               5                  10                  15

Glu Thr Ala Thr Leu Ser Cys Arg Ala Ser Gln Ser Val Arg Ser Tyr
             20                  25                  30

Leu Ala Trp Tyr Gln Gln Lys Pro Gly Gln Ala Pro Arg Leu Leu Ile
         35                  40                  45

Tyr Gly Ala Ser Thr Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Tyr Ser Ser Trp Tyr Thr
                 85                  90                  95

Phe Gly Gln

<210> SEQ ID NO 7
<211> LENGTH: 111
<212> TYPE: PRT
<213> ORGANISM: human

<400> SEQUENCE: 7

Gln Val Gln Leu Gln Glu Ser Gly Gly Leu Val Gln Pro Gly Gly
 1               5                  10                  15

Ser Leu Arg Leu Ser Cys Ala Ala Ser Glu Phe Thr Phe Ser Asn Tyr
             20                  25                  30

Tyr Met Ser Trp Val Arg Gln Ala Pro Gly Lys Gly Leu Glu Trp Val
         35                  40                  45

Ser Tyr Ile Ser Tyr Asp Gly Gly Ser Thr Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Ala Trp Arg Leu Ser Ala Arg Ala Gly Tyr Phe Asp Tyr
            100                 105                 110

<210> SEQ ID NO 8
<211> LENGTH: 100
<212> TYPE: PRT
<213> ORGANISM: human

<400> SEQUENCE: 8

Glu Leu Thr Leu Thr Gln Ser Pro Ser Ser Leu Ser Ala Ser Val Gly

```
                1               5                  10                 15
Asp Arg Val Thr Ile Thr Cys Arg Ala Ser Gln Asp Ile Arg Gly Tyr
                        20                  25                 30

Leu Ala Trp Tyr Gln Gln Lys Pro Gly Lys Ser Pro Arg Leu Leu Ile
             35                  40                  45

Tyr Ser Ala Ser Thr Leu Gln Thr Gly Val Pro Ser Arg Phe Ser Gly
         50                  55                  60

Ser Arg Ser Gly Thr Asp Tyr Thr Leu Thr Ile Ser Ser Leu Gln Ser
 65                  70                  75                  80

Glu Asp Val Ala Thr Tyr Tyr Cys Gln Gln His Tyr Ser Thr Pro Leu
                     85                  90                  95

Thr Phe Gly Gln
            100

<210> SEQ ID NO 9
<211> LENGTH: 108
<212> TYPE: PRT
<213> ORGANISM: human

<400> SEQUENCE: 9

Glu Val Gln Leu Val Glu Ser Gly Gly Leu Val Gln Pro Gly Gly
 1               5                  10                  15

Ser Leu Arg Leu Ser Cys Ala Ala Ser Gly Phe Thr Phe Ser Asp Tyr
             20                  25                  30

Tyr Val Asn Trp Val Arg Gln Thr Pro Gly Lys Gly Pro Glu Trp Val
             35                  40                  45

Gly Phe Ile Arg Asn Lys Ala Asn Gly Gly Thr Ala Glu Tyr Ala Ala
         50                  55                  60

Ser Val Lys Gly Arg Phe Thr Ile Ser Arg Asp Asp Ser Lys Asn Ser
 65                  70                  75                  80

Leu Tyr Leu Gln Met Ser Gly Leu Lys Thr Glu Asp Thr Ala Val Tyr
                     85                  90                  95

Tyr Cys Ile Leu Ser Asp Thr Gly Ala Phe Asp Val
                100                 105

<210> SEQ ID NO 10
<211> LENGTH: 99
<212> TYPE: PRT
<213> ORGANISM: human

<400> SEQUENCE: 10

Glu Leu Val Met Thr Gln Ser Pro Ala Thr Leu Ser Leu Ser Pro Lys
 1               5                  10                  15

Glu Thr Ala Thr Leu Ser Cys Arg Ala Ser Gln Ser Val Arg Ser Tyr
             20                  25                  30

Leu Ala Trp Tyr Gln Gln Lys Pro Gly Gln Ala Pro Arg Leu Leu Ile
             35                  40                  45

Tyr Gly Ala Ser Thr Arg Ala Thr Gly Ile Pro Ala Arg Phe Ser Gly
         50                  55                  60

Ser Gly Tyr Gly Thr Asp Phe Thr Leu Thr Ile Ser Ser Leu Glu Pro
 65                  70                  75                  80

Glu Asp Phe Ala Val Tyr Tyr Cys Gln Gln Tyr Ser Ser Trp Tyr Thr
                     85                  90                  95

Phe Gly Gln

<210> SEQ ID NO 11
```

```
<211> LENGTH: 107
<212> TYPE: PRT
<213> ORGANISM: human

<400> SEQUENCE: 11

Gln Val Gln Leu Gln Glu Ser Gly Gly Gly Leu Ala Lys Pro Gly Gly
  1               5                  10                  15

Ser Leu Arg Leu Thr Cys Ala Ala Ser Gly Phe Thr Phe Ser Asp Tyr
             20                  25                  30

Trp Met Ser Trp Val Arg Gln Ala Pro Gly Lys Gly Leu Glu Trp Val
         35                  40                  45

Gly Glu Ile Asn Pro Asp Gly Gly Arg Thr Asn Tyr Lys Asp Phe Val
     50                  55                  60

Lys Gly Arg Phe Thr Ile Ser Arg Asp Asn Ala Lys Asn Thr Leu Tyr
 65                  70                  75                  80

Leu Gln Leu Asn Ser Leu Lys Thr Glu Asp Thr Ala Ile Tyr Tyr Cys
                 85                  90                  95

Thr Gly Ala Gly Pro Thr Tyr Tyr Phe Asp Tyr
            100                 105

<210> SEQ ID NO 12
<211> LENGTH: 100
<212> TYPE: PRT
<213> ORGANISM: human

<400> SEQUENCE: 12

Glu Leu Val Met Thr Gln Ser Pro Ser Ser Leu Phe Ala Ser Ile Gly
  1               5                  10                  15

Asp Arg Val Thr Ile Thr Cys Arg Ala Ser Gln Asn Ile Arg Ser Asn
             20                  25                  30

Leu Ala Trp Tyr Gln Gln Lys Pro Gly Lys Thr Pro Arg Leu Leu Ile
         35                  40                  45

Tyr Asp Ala Ser Ser Leu Gln Pro Gly Ile Pro Ser Arg Phe Ser Gly
     50                  55                  60

Ser Gly Ser Gly Thr Tyr Tyr Thr Leu Thr Ile Ser Ser Leu Gln Ser
 65                  70                  75                  80

Asp Asp Leu Ala Thr Tyr Tyr Cys Gln Gln Gly Tyr Thr Thr Pro Val
                 85                  90                  95

Thr Phe Gly Gln
            100
```

RECOMBINANT ANTIBODY FRAGMENTS AS AUTOANTIBODY ANTAGONISTS

CROSS REFERENCE TO RELATED APPLICATION

This application is a continuation and claims priority under 35USC120 to U.S. Ser. No. 09/691,654, filed Oct. 17, 2000, now abandoned.

GOVERNMENTAL RIGHTS

This invention was made with Government support under Grant No. AI 43073, awarded by the National Institutes of Health. The Government has certain rights in this invention.

INTRODUCTION

1. Field of the Invention

The field of this invention is polypeptide autoantibody inhibitors and methods of use thereof.

2. Background

Multiple sclerosis (MS) is a chronic relapsing remitting disorder disease of the central nervous system that affects 350,000 Americans and, second to trauma, is the leading cause of disability among young adults. MS is an immune-mediated disorder characterized pathologically by perivenular white matter infiltrates comprised of macrophages and mononuclear cells (inflammation), and destruction of the myelin sheaths that insulate nerve fibers (demyelination).

Experimental allergic encephalomyelitis (EAE) in rodents has been the most widely employed model for testing of therapies for human MS. These traditional disease models for MS generally have promoted the concept that MS is a T-cell-mediated disorder. However, the autoantigens that serve as targets for the immune attack have not been identified and the molecular mechanisms implicated in myelin damage remain uncertain. While it is clear that CNS inflammation in EAE is initiated by autoaggressive T-cells that recognize myelin antigens in the context of class II-MHC molecules, many of the models lack the early demyelinating component of the MS lesion. B-cell activation and antibody responses appear necessary for the full development of EAE and earlier studies on immune mediated demyelination using myelinated cultures of CNS tissue have implicated humoral factors as effector mechanisms. Thus, it is not surprising that rodent EAE has not been a robust predictor of efficacy in humans as fundamental differences in the clinical course, pathology, and immunologic response to myelin proteins distinguish rodent EAE from human MS.

Recently a novel MS-like illness in an outbred nonhuman primate, the common marmoset *Callithrix jacchus*, has been defined. The marmoset EAE has a prominent, MS-like early demyelinating component which requires the presence of myelin-specific autoantibodies, and has afforded an opportunity to understand the interactions between these antibodies and their target antigens on myelin. Characteristics of the model include: a. Mild clinical signs and a relapsing remitting course similar to MS; b. A primary demyelinating pathology with early gliosis indistinguishable from MS lesions (demyelinating plaques); c. Natural bone marrow chimerism permitting successful adoptive transfer of encephalitogenic (e.g. disease-inducing) T-cell clones and lines; d. Diversity of the encephalitogenic repertoire of T-cells reactive against the major myelin protein myelin basic protein (MBP); e. Different disease phenotypes resulting from immunization with different myelin constituents: in contrast to whole myelin, immunization with MBP produces a non-demyelinating form of EAE; f. Demonstration that demyelination is antibody-mediated but also requires an encephalitogenic T-cell response to facilitate autoantibody access to the nervous system; and, g. A key role of myelin oligodendrocyte glycoprotein (MOG) in plaque formation: adoptive transfer of anti-MOG antibody in non-demyelinating MBP-EAE reproduces fully developed MS-like pathology.

The highly immunogenic properties of MOG (<0.05% of total myelin protein) may be related to its extracellular location on the outermost lamellae of the myelin sheath, where it is accessible to pathogenic antibody in the context of blood brain barrier disruption by encephalitogenic T-cells. The *C. jacchus* model permits precise identification of cellular and humoral immune responses that result in an MS-like lesion in a species with immune and nervous system genes that are 90–95% homologous to humans. The relevance of this model to human MS is emphasized by the recent finding of strong T-cell and antibody responses to MOG in MS patients.

Auto-antibodies against MOG have been shown to be present in demyelinating lesions in the brain of patients with multiple sclerosis (MS) and *C. jacchus* primates with MOO induced experimental allergic encephalomyelitis (EAE). Furthermore, anti-MOG antibodies have been demonstrated to be essential for the development of demyelinating lesions in *C. jacchus* EAE Additionally, it was shown, that ultra-structural features of demyelinating lesion are virtually indistinguishable between marmosets and humans MOG specific F[ab']2 fragments obtained by pepsin digestion of polyclonal anti-MOG antibodies from MOG immunized *C. jacchus* were previously shown to be able to counteract the development of demyelination in *C. jacchus* animals. See U.S. Ser. No. 09/384,036, now U.S. Pat. No. 6,333,033, and related PCT/US99/19546. However, no information is available to date on the molecular diversity, neither of pathogenic antibodies in *C. jacchus* EAE, nor of F[ab']2 fragments able to act as their antagonists.

SUMMARY OF THE INVENTION

The invention provides methods and compositions for inhibiting autoantibody binding in demyelinating disease. The compositions comprise immunoglobulin CDR3 sequences derived from combinatorial phage display libraries selected for high-affinity MOO binding MOG-specific CDR3 sequences include heavy chain CDR3 sequences selected from the group consisting of SEQ ID NOS:1, 3, 5, 7, 9 and 11 and light chain CDR3 sequence selected from the group consisting of SEQ ID NOS:2, 4, 6, 8, 10 and 12. In particular embodiments, the heavy chain CDR3 sequence is SEQ ID NO:1; the heavy chain is within a $V_H1$ variable region subfamily domain or a $V_H3$ variable region subfamily domain; the light chain CDR3 sequence is SEQ ID NO:2; and the light chain is within a VκIII variable region subfamily domain or a VκI variable region subfamily domain. In a particular embodiment, the polypeptide comprises both heavy chain CDR3 sequence selected from the group consisting of SEQ ID NOS:1, 3, 5, 7, 9 and 11 and a second light chain CDR3 sequence selected from the group consisting of SEQ ID NOS:2, 4, 6, 8, 10 and 12. The CDR3 sequences may be incorporated into a wide variety of polypeptides, so long as the requisite MOG binding is maintained. In a preferred embodiment, the polypeptide is an F(ab).

The invention provides pharmaceutical compositions comprising a polypeptide according to claim 1 and a pharmaceutically acceptable carrier and use of the subject compositions in methods for inhibiting MOG-antibody binding. In general, these methods comprise the step of contacting a mixture of a MOG and an antibody with a subject polypeptide, whereby the MOG-antibody binding is inhibited. In a particular application, the method is a method of inhibiting demyelination associated with the binding of an autoantibody to a myelin oligodendrocyte glycoprotein (MOG) polypeptide, comprising the step of administering to a marmoset or human host, subject to a pathogenic MOG polypeptide-polyclonal autoantibody binding, an effective amount of a composition comprising a subject polypeptide not having a functional Fc portion and sufficient to specifically bind the MOG polypeptide and competitively inhibit the binding of the autoantibody to the MOG polypeptide, whereby the demyelination is inhibited. In more specific embodiments, the administered composition further comprises a MOG tolerogenic T-cell epitope. The method may also be practices with a composition comprising a plurality of subject polypeptides, wherein each of the plurality of polypeptides specifically binds a different MOG eptiope.

DETAILED DESCRIPTION OF THE INVENTION

The following description and examples are offered by way of illustration and not by way of limitation.

Methods of making antibody fragments, particularly F(ab) are known in the art. (See for example, Harlow and Lane, Antibodies: A Laboratory Manual, Cold Spring Harbor Laboratory, New York (1988), incorporated herein by reference). The subject polypeptides may be provided uncomplexed with other protein, complexed in a wide variety of non-covalent associations and binding complexes, complexed covalently with other peptide sequences (homo or hetero-chimeric proteins), etc.

Molecular and biochemical methods are available for biochemical synthesis, molecular expression and purification of the subject compositions, see e.g. Molecular Cloning, A Laboratory Manual (Sambrook, et al. Cold Spring Harbor Laboratory), Current Protocols in Molecular Biology (Eds. Ausubel, et al., Greene Publ. Assoc., Wiley-Interscience, NY) or that are otherwise known in the art. Material and methods for the expression of heterologous recombinant proteins in bacterial cells (e.g. *E. coli*), yeast (e.g. *S. Cerevisiae*), animal cells (e.g. CHO, 3T3, BHK, baculovirus-compatible insect cells, etc.) are well-known. The amino acid sequences of the disclosed polypeptides are used to back-translate polypeptide-encoding nucleic acids optimized for selected expression systems (Holler et al. (1993) Gene 136, 323–328; Martin et al. (1995) Gene 154, 150–166).

In the preparation of the pharmaceutical compositions of this invention, a variety of vehicles and excipients and routes of administration may be used, as will be apparent to the skilled artisan. Representative formulation technology is taught in, inter alia, Remington: The Science and Practice of Pharmacy, 19th ed., Mack Publishing Co., Easton, Pa., 1995; e.g. *Goodman & Gilman's The Pharmacological Basis of Therapeutics*, 9th Ed., 1996, McGraw-Hill.

Combinatorial recombinant libraries were made in order to generate F(ab) fragments with high affinity for MOG capable of competing with pathogenic IgG and of inhibiting complement-mediated and antibody dependent cellular cytotoxicity. These F(ab) fragments were tested alone and in combination with T-cell tolerogenic peptides for their ability to prevent and treat disease in *C. jacchus*.

A recently identified patient with a progressive spinal cord disorder associated with an IgG monoclonal gammopathy reactive to MOG offered a unique example of the pathophysiologic consequences of an anti-MOG antibody response in a natural experiment. The human monoclonal antibody was adoptively transferred into a *C. jacchus* with non-demyelinating EAE. Following adoptive transfer the marmoset developed demyelination. Transfer of human IgG in this species is well-tolerated and the blocking ability of F(ab) fragments is demonstrated in the adoptive transfer system. The antibody fragments retain their ability to recognize antigenic epitopes yet lack the ability to activate complement or bind macrophages, they coat the autoantigen such that the endogenous autoantibodies are unable to bind a pathological level.

Recombinant CDR3 Containing MOG-binding Polypeptides

The construction of a combinatorial library is achieved by randomly recombining all VH and V kappa sequences in a vector suitable for the expression of F[ab] fragments on the surface of a phage particle, attached to the gIII protein. After selection of MOG-specific F[ab] clones by panning, we removed the gIII protein gene to be able to express soluble MOG-specific F[ab] fragments. This approach permitted both DNA sequencing, and immunological characterization of individual F[ab] fragments.

DNA sequence analysis revealed a predominant use of the VH1 subfamily. From a total total of sixty distinct F[ab] fragments analyzed, 57 were of the VH1 subfamily and 3 the VH3 subfamily. This result demonstrates that usage of heavy chain variable region genes in the antibody response against the MOG antigen, is highly restricted.

TABLE 1

| $V_H$ and $V\kappa$ subfamily usage | | | |
|---|---|---|---|
| $V_H$Subfamily | Vκ Subfamily | No. Clones | % Clones |
| $V_H1$ | VκIII | 57 | 95 |
| $V_H3$ | VκI | 2 | 3 |
| $V_H3$ | VκIII | 1 | 2 |

Table 1 shows the frequencies of VH and V kappa subfamily usage. Only three combinations of VH and V kappa subfamilies were found. The distribution of VH and V kappa subfamilies is clearly dominated by combinations of VH1 and V kappa III. Other, less frequent combinations of VH3 with V kappa I and III were also found. This data demonstrates, that few combinations of heavy and light chain variable region genes are necessary to generate the antibody repertoire against MOG.

TABLE 2

Diversity in the Antigen Binding Domains: MOG-Fab $V_H$ and Vk-subfamily usage and H/kL-CDR motifs. The far right column shows the respective clone number and the SEQ ID NOS for the corresponding heavy and light chain, respectively. Under each CDR sequence is the corresponding SEQ ID NO boundaries.

H chain

| $V_H$ | CDR1 | CDR2 | CDR3 | |
|---|---|---|---|---|
| $V_H 1$ | SYAIS | AFDPEYGSTTYAQKFQG | CARDVNFGNYFDY | |
| | res. 31–35 | res. 50–66 | res. 96–108 | |
| $V_H 1$ | SYAIS | GVDPEYGGTTYTQKFQG | CARDRGMGNYFDY | |
| | res. 31–35 | res. 50–66 | res. 96–108 | |
| $V_H 1$ | SYGMQ | WINTNTGGTSYAQKFQG | CARDATRILADVLDY | |
| | res. 31–35 | res. 50–66 | res. 96–110 | |
| $V_H 3$ | SNYYMS | YISYDGGSTYYADSVKG | CARAWRLSARAGYFDY | |
| | res. 30–35 | res. 50–66 | res. 96–111 | |
| $V_H 3$ | SDYYVN | FIRNKANGGTAEYAASVKG | CILSDTGAFDV | |
| | res. 30–35 | res. 50–68 | res. 98–108 | |
| $V_H 3$ | SDYWMS | EINPDGGRTNYKDSVKG | CTGAGPTYYFDY | |
| | res. 30–35 | res. 50–66 | res. 96–107 | | kL chain

| Vk | CDR1 | CDR2 | CDR3 | | |
|---|---|---|---|---|---|
| VkIII | RAGQSVSYYLA | GASTRAT | CQQYSSWPPTF | M26 | |
| | res. 24–34 | res. 50–56 | res. 88–98 | SEQ ID NO: 1/2 | |
| VkIII | RASQSVSSYLA | GASTRAT | CQQYSSWPLTF | M38 | |
| | res. 24–34 | res. 50–56 | res. 88–98 | SEQ ID NO: 3/4 | |
| VkIII | RASQSVRSYLA | GASTRAT | CQQYSSWYTF | M45 | |
| | res. 24–34 | res. 50–56 | res. 88–97 | SEQ ID NO: 5/6 | |
| VkI | RASQDIRGYLA | SASTLQT | CQQHYSTPLTF | M3-8 | |
| | res. 24–34 | res. 50–56 | res. 88–98 | SEQ ID NO: 7/8 | |
| VkIII | RASQSVRSYLA | GASTRAT | CQQYSSWYTF | M3-24 | |
| | res 24–34 | res. 50–56 | res. 88–97 | SEQ ID NO: 9/10 | |
| VkI | RASQNIRSNLA | DASSLQP | CQQGYTTPVTF | M3-31 | |
| | res. 24–34 | res. 50–56 | res. 88–98 | SEQ ID NO: 11/12 | |

Among the 60 analyzed clones, we identified 6 different H chain CDR3 motifs and 5 different kappa L chain CDR3 motifs (shown in bold in Table 2—the corresponding complete antigen binding region shown are provided as SEQ ID NOS:1–12, respectively). The Heavy chain CDR3 shows a great degree of variability, both in length and sequence, while the L chain CDR3 did not appear to be mutated to the same extent. 73% of all clones contained the two CDR3 motifs listed first. This data shows that the antibody response against MOG, which is restricted in its Variable region subfamily usage, is diverse in its antigen binding properties.

In contrast to what was previously shown for polyclonal serum Abs from MOG immunized animals, monoclonal F[ab]s did not recognize linear peptides of MOG; significant binding was only found when the whole extracellular domain of MOG was present. Using immunohistochemical staining of brain tissue, we were able to show that MOG-specific F[ab] fragments also bind to the native protein on the myelin sheath. We found specific staining of oligodendrocytes and myelin by a biotin labeled F[ab] fragment selected from the combinatorial library and no such staining was observed in the negative control.

We also found that the recombinant F[ab] fragments were able to compete against affinity purified anti-MOG Abs from C. jacchus immunized with MOG. Displacement curves between C. jacchus anti-MOG Abs and different F[ab] fragments revealed that the amount of biotin labeled anti-MOG antibodies bound to rMOG is displaced by increasing concentrations of F[ab] fragments. In contrast, the individual F[ab] fragments were unable to compete against each other, indicating different conformational epitopes. This combinatorial analysis indicates that the antibody response against the MOG antigen is restricted in its usage of VH and V kappa subfamilies, yet diverse in its antigen binding sites. In sum, the recombinant F[ab] fragments: recognize different conformational epitopes of the MOG molecule; bind to native MOG on intact myelin; and efficiently compete against native anti-MOG Abs.

Induction of Marmoset EAE. EAE was induced in marmosets as described by Genain et al. (1999) Nature Medicine 5, 170–175. Six marmosets were actively sensitized with 50 to 100 μg of recombinant rat MOG dissolved in 100 μl of phosphate-buffered saline and emulsified with an equal volume of complete Freund's adjuvant (CFA) containing 3 mg/ml killed Mycobacterium tuberculosis (h37Ra; DIFCO, Detroit, Mich.). The MOG/CFA emulsion was given intradermally at four injection sites in the scapular and hip regions in a total volume of 0.2 ml. On the day of immunization with MOG/CFA, $1 \times 10^{10}$ inactivated Bordetella pertussis organisms in 2.5 ml of isotonic saline were given intravenously and the dose repeated 2 days later. For comparison, 4 marmosets sensitized with 200 mg of whole white matter (WM)/CFA and B. pertussis were examined between 18 and 39 days after immunization. MOG-sensitized marmosets were maintained for up to 93 days after immunization. Animals sensitized with either WM or MOG displayed signs of EAE within 21 days of immunization. The animals were sacrificed by intracardiac perfusion under deep anesthesia 18 to 93 days after immunization.

MS tissues from humans. Human CNS tissues were obtained from 3 subjects with MS by biopsy or autopsy (8 weeks, 11 years and 17 years after diagnosis). Patient 1 was an 18-year old Caucasian woman with a 3-month history of acutely developing right hemiplegia, sensory loss, and spasticity. Computed tomographic scanning revealed WM hypodensity in the left parieto-occipital region. A brain biopsy was performed for neuropathological evaluation. The resultant diagnosis was actively demyelinating, inflammatory, edematous lesions of recent origin, typical of a fulminant inflammatory demyelinating condition, consistent with acute MS.

Patient 2 was a 31 year old Caucasian female with an 8-year history of chronic progressive MS characterized by numbness and weakness of the limbs, gait disturbance, urinary incontinence, tremor, nystagmus, and blurred vision. Terminally, the patient was wheelchair-bound, developed seizures and aspiration pneumonia, and died. An autopsy was performed within 1.5 hours of death. Neuropathological examination revealed a predominance of small (3–5 mm), disseminated, recent, intensely inflamed, edematous, demyelinating lesions as well as larger, more established plaques with fibrous astrogliosis and well-demarcated edges.

Patient 3 was a 34-year old Caucasian female with a history of relapsing-remitting MS for 10 years after initial diagnosis at age 20. The disease entered a chronic progressive course for the last 7 years of her life. At the time of death, the patient presented with bilateral optic atrophy, internuclear ophthalmoplegia, spastic paraparesis, and moderate limb ataxia. The cause of death was respiratory failure. An autopsy was performed 4 hours after death. Neuropathology of this case revealed intensely inflammatory, edematous, actively demyelinating lesions of recent origin, as well as active chronically demyelinated lesions.

Tissue Preparation for Analysis. At the time of sampling, animals were sacrificed under pentobarbital anesthesia by intracardiac perfusion with 200 ml of phosphate-buffered saline followed by 150 to 200 ml of cold $PO_4$-buffered 2.5% glutaraldehyde. Two MOG-sensitized marmosets were sampled during the acute phase of the disease (14–16 days after immunization), 3 were taken after the acute phase, either during relapses or remission (23, 25 and 27 days after immunization), and 1 was examined after two relapses at 93 days after immunization. The 4 whole WM-sensitized animals were examined at 18, 30, 30 and 39 days after immunization after acute onset but before relapse. From the glutaraldehyde-perfused animals, the CNS was removed and routine neuropathology performed on formalin postfixed, paraffin-embedded material stained with hematoxylin and eosin, Lusol Fast Blue (for myelin), and the Bodian silver technique (for axons).

For fine structural analysis of marmoset tissues, 1-mm slices were taken form optic nerve, cerebral hemispheres, cerebellum, brainstem, medulla, and spinal cord at C7, T3, L2, L5, L6, and L7. In addition, samples were taken from spinal nerve roots and sciatic nerves. The slices of glutaraldehyde-fixed brain tissue were trimmed as flat rectangles (~4×6 mm) and spinal cord was left as whole slices. From the 3 cases of MS describe in Example 2, small pieces of biopsy tissue or slices of autopsied CNS material, 3 to 5 mm thick, were immersion-fixed for 4 to 24 hours at 4° C., then cut into thin, 1-mm slices to 3 to 5 mm in diameter. Glutaraldehyde-fixed tissues were then postfixed in $PO_4$-buffered 1% $OsO_4$ for 1 hour on ice. Samples were dehydrated, cleared in propylene oxide, and embedded flat in epoxy resin. Thin (1 $\mu$m) sections of epoxy-embedded tissue were prepared for light microscopy (LM) and stained with toluidine blue or reacted for immunocytochemistry. For electron microscopy (EM), sections were placed on copper grids, contrasted with lead and uranium salts (lead citrate and uranyl acetate), carbon-coated, and scanned in a Siemens 101 or Hitachi H 600-S.

Ultrastructural patterns of demyelination are identical in *C. jacchus* EAE and in acute MS plaques. CNS tissues from 6 *C. jacchus* marmosets with MOG-induced EAE and from 3 human subjects with MS, all showing acute lesions, were examined by electron microscopy (EM). In marmoset EAE, large demyelinated plaques up to several mm in diameter were disseminated throughout the CNS, invariably centered on venules and characterized by perivascular inflammation and a prominent margin along which many myelinated nerve fibers displayed vacuolated myelin sheaths. This typical pattern of myelin vacuolation resulted from the enlargement of individual myelin sheaths due to interlamellar splitting and swelling, with the axon displaced to one side surrounded by several layers of intact myelin. Micrographs showing the optic nerve from an animal with acute EAE induced by immunization with 50 $\mu$g of recombinant rat MOG in adjuvant, sacrificed 3 days after onset of clinical signs demonstrated the presence of large intramyelinic vacuoles at the perimeter of a demyelinated lesion, with axons surrounded by normal-appearing myelin sheaths elsewhere.

Between the lesion center and the margin was a broad zone of demyelination containing macrophages laden with myelin debris. The most striking finding was the presence within the demyelinated zone of large numbers of axons surrounded by aggregates of disrupted myelin rearranged as an expanded network. These axons were displaced laterally as the membranous network gradually became dissociated from the axon and taken up by adjacent macrophages.

Demyelination of fibers in acute MS was structurally identical to that seen in marmoset EAE, with the demyelinated axon lying within a membranous network of myelin. Elsewhere in the edematous parenchyma, free floating aggregates of myelin debris were common. Electron photomicrographs of tissue taken from a subcortical white matter biopsy from an 18-year old female patient with an 8-week history of neurologic signs, white matter hypodensity on MRI scan and a diagnosis of acute MS showed myelin around axons transformed into a vesicular network similar to that described above. Fibrous astroglial processes, naked axons and a reactive, ameboid microglial cell (below), were also identified. High resolution analysis of the myelin networks in both marmoset EAE and human MS revealed vesicles surrounded by 2 to 3 layers of loosely compacted membranes with a reduced periodicity (5–6 nm) when compared to intact myelin in normal tissue.

MOG-specific autoantibodies are associated with myelin vesiculation in the *C. jacchus* EAE lesion. MOG is a quantitatively minor myelin protein (less than 0.05% of total myelin proteins) with an immunoglobulin (Ig)-like extracellular domain that is expressed in abundance on the outermost layer of myelin sheaths, which may render it accessible to antibody attack. Although autoantibodies against MOG have been shown to enhance demyelination in several EAE models, the detailed interactions between these antibodies and myelin membranes has not been investigated. To identify the sites of autoantibody binding within demyelinating lesions, we performed immunocytochemistry on frozen and epoxy-embedded marmoset CNS tissue with gold-labeled anti-human IgG antibody (cross-reactive with marmoset IgG) followed by silver enhancement.

For the demonstration of antigen-specific autoantibodies in marmoset and human MS tissue in situ, a selection of myelin-related and control peptides were directly coupled to immunogold and applied to tissue sections. Immunogold labeling was performed on ultra-thin sections of frozen or fixed tissues. Gold conjugates were prepared of (1) three MOG peptides (amino acids [aa] 1–20, aa 21–40, and aa 41–60 of human MOG) with known encephalitogenic activity in marmosets; (2) one MOG peptide that has been shown not to be encephalitogenic in marmosets (aa 101–120); (3) one human myelin basic protein (MBP) peptide (aa 82–101) that is encephalitogenic in marmosets and immunodominant in humans with the DR2 haplotype; and, as a control, (4) a peptide of mouse serum albumin (MSA; aa 560–574). Peptides having human MOG subsequences were synthesized using standard Fmoc chemistry and purified (>95%) by HPLC (Research Genetics Inc., Huntsville, Ala.): MOG 1–20, MOG 21–40, MOG 61–80, MBP 82–101, and MSA 560–574. The gold conjugates were synthesized by using monosulfo-N-hydroxy succinimide-Nanogold labeling reagent (particle diameter, 1.4 nm), according to the manufacturer's instructions (Nanoprobes, Stonybrook, N.Y.), followed by extensive dialysis to remove unreacted peptide. Immunoreactivity was detected on 1-$\mu$m epoxy sections of marmoset spinal cord tissue and active MS lesions. For this, sections were etched with sodium ethoxide, equilibrated in $PO_4$-buffered saline containing 0.05% Triton X-100, and blocked with 10% normal rabbit serum. Sections were incubated with peptide-immunogold conjugates (1:100 in buffer) for 2 hours at room temperature. After washing, detection was performed by using silver enhancement (Nanoprobes). Sections were counterstained with toluidine blue. For the detection of IgG, sections were reacted with gold-labeled anti-monkey or anti-human IgG (Nanoprobes) at 1:100.

As controls, sections were either pretreated with unlabeled encephalitogenic MOG peptides or MBP to block the reaction, reacted with unlabeled nonencephalitogenic MOG peptide (aa 101–120) before application of the gold conjugates, or treated with gold-labeled irrelevant antigens (histone or MSA) or irrelevant IgG (anti-goat). The specificity of the labeling with the gold conjugates of encephalitogenic MOG peptides was also assessed in western blots where the MOG protein was first reacted with immune marmoset serum. Full details of the test and control reagents used to determine the specificity of the immunoreactivity can be found in Genain et al., Nature Med. 5:170–175 (1999).

Sections from the lumbar region of the spinal cord from the animals were obtained. The positive reactivity of vesiculated mydin around axons indicated the presence of IgG. Non-demyelinating axons did not stain. Positive reactivity for IgG was specifically found over the vesiculated networks of disrupted myelin surrounding axons.

We next identified the target antigens bound by these immunoglobulins by the application of immunogold-labeled conjugates of selected peptides of MOG and myelin basic protein (MBP). These myelin antigens were directly labeled with the gold particles on their primary $NH_2$ residues and were used to detect antigen-specific autoantibody in situ. With this technique, three separate gold-conjugated peptides of MOG were co-localized over the networks of disintegrating myelin sheaths in a pattern similar to that observed for gold-conjugated anti-IgG.

These peptides contained the amino acid sequences of MOG recognized by demyelinating antibodies that develop in serum of MOG-immunized marmosets (aa 1–20, aa 21–40 and aa 61–80). The gold-conjugated MOG peptide (aa 21–40) used has a sequence conserved across species. MOG-reactive droplets were also seen in surrounding macrophages, indicating the presence of internalized myelin debris to which anti-MOG antibody was bound. Positive reactivity with the labeled antigen indicated the presence of MOG-specific antibody in situ on vesicular myelin around axons and on myelin debris within the extracellular space and macrophages. Normal myelin (around the majority of the fibers) was not stained.

In contrast, gold-labeled conjugates of a peptide containing an immunodominant epitope of human MBP (aa 82–101, conserved across primate species) and of a control peptide of mouse serum albumin (MSA, aa 560–574), failed to label myelin membranes or macrophages. Thus, the vesiculated myelin networks are unstained by either the gold-conjugated peptide of MBP or the gold-conjugated peptide of MSA.

These observations demonstrate in this non-human primate model of EAE that antibodies specific to MOG are in direct contact with the disintegrating myelin membranes and indicate that formation of the vesiculated membranous networks resulted from lytic attack by these autoantibodies.

MOG-specific autoantibodies are associated with myelin vesiculation in lesions of acute human MS. We next investigated with similar immunogold labeling the presence of MOG- and MBP-specific autoantibodies in CNS tissue obtained at biopsy or autopsy from patients with MS. As in marmoset EAE, gold-conjugated anti-IgG labeled the membranous myelin networks around single demyelinating axons, along with droplets of myelin debris scattered throughout the parenchyma. IgG is localized along the disintegrated myelin sheath of an axon cut in longitudinal section; cytoplasm of an hypertrophied astrocyte; tangential section of an oligodendrocyte. Densely stained IgG-coated myelin debris are visible in the parenchyma and in 3 macrophages (probably ameboid microglia) In addition, occasional plasma cells showed positive staining by anti-IgG. With the immunogold-labeled myelin antigen conjugates, vesiculated myelin networks were intensely stained by gold-conjugated-MOG peptides, and to a lesser extent by gold-conjugated MBP but not by MSA.

IgG-myelin complexes labeled with gold-conjugates of MOG and MBP were also present in macrophages but not in astrocytes or oligodendrocytes. No MOG- or MBP-labeled plasma cells were encountered. Reactivity with gold-conjugates was not observed in normal appearing MS white matter or around perivascular inflammatory cuffs. In marmosets immunized against whole myelin, a similar pattern of both anti-MOG and anti-MBP Ig deposition was observed. CNS tissue from amyotrophic lateral sclerosis, another neurologic disorder associated with white matter damage and macrophage activity, failed to show myelin antigen-specific immunogold reactivity. These findings directly identify MOG-specific antibodies in actively demyelinating lesions of human MS, indicating that, as in MOG-induced EAE, these autoantibodies play a causal role in the formation of small vesicles in the disrupted myelin sheaths. Soluble and B-cell surface Ig with anti-MBP specificity have been described in MS brain tissue, and in the current study, MBP-specific Ig was localized within the vesiculated myelin networks in MS lesions. Although anti-MBP antibodies have not been shown experimentally to initiate demyelinating pathology, these autoantibodies can mediate separate pathogenic mechanisms such as receptor-mediated phagocytosis by macrophages and/or presentation of myelin autoantigens to specific T-cells.

It is noteworthy that autoantibodies appear to be bound exclusively to the small vesicles that characterize the stage of complete disintegration of the myelin membranes, and to the myelin debris present either in the extracellular space or in phagocytic cells. Interestingly, similar but less extensive vesiculation of myelin was reported in earlier studies of rodent EAE where it was perceived as a transient early phenomenon. However, in the marmoset where lesion formation is protracted and ever expanding, the disrupted myelin was found consistently. The large scale vacuolation of myelin at the lesion margin among normally myelinated fibers occurred in the absence of significant local cellular infiltration or IgG deposition, and has also been reported at the edge of active MS lesions. This change in the myelin structure could be mediated by soluble factors diffusing from the center of the demyelinating plaque or from activated glial cells at the edge of the lesion. Morphologic changes similar to these large vacuoles have been reported in myelinated CNS cultures exposed to TNF-alpha and to a lesser degree, in cultures exposed to serum from animals with EAE and from subjects with MS.

Many of the therapeutic approaches targeting pathogenic T-cell responses in EAE models have not yet translated into successful treatment for human MS, perhaps suggesting that other components of the immune system need to be taken into account. B-cell responses appear to be a key factor for severity of clinical disease and pathology in C. jacchus EAE. The current results underscores the role of autoantibodies in the widespread destruction of myelin in MS, and emphasizes that in diseases that are initiated by T-cell responses, antibodies against critical antigens of the target organ are essential for development of irreversible tissue damage.

In vivo Administration of MOG-specific recombinant F(ab) Fragments. Here we show that recombinant antibody fragments against MOG may be used as therapeutic tools to competitively block the binding of real-life, pathogenic antibody. In a particular example, marmosets are first sensitized to EAE with MBP (non-demyelinating), then both given intravenous demyelinating antibody against MOG. Simultaneously, one animal (control) receives a placebo F(ab) injection, and the other receives recombinant F(ab) fragments. The control animal shows aggravation of the clinical signs of EAE and the experimental animal do not. The animals are sacrificed 3–5 days later and histology of the brain and spinal cord obtained. The control animal have evidence of demyelinating lesions, and the experimental animal have lesions with inflammation (cellular infiltration) but no demyelination (no myelin destruction). This experiment shows that marmosets can be protected from antibody mediated demyelination by MOG-specific recombinant F(ab) fragments.

Marmosets are administered 1 mg MBP in CFA containing B. Pertussis at Day 0 inducing non-demyelinating EAE. On Day 21 the animals were administered intravenously 0.17 mmol/kg of a recombinant MOG-specific F(ab) or an anti-Influenza-A (control) antibody, then administered 0.17 mmol/kg 8.18.C5 antibody followed by a second intravenous administration of the F(ab) for two hours. The animals were euthanized on day 35. Tissue samples were prepared as described in Example 3. Using high resolution microscopy and immunogold-labeled peptides of myelin antigens capable of detecting antigen-specific antibodies in situ, we have identified autoantibodies specific for myelin/oligodendrocyte glycoprotein (MOG) around individual demyelinating axons in acute lesions of both human MS and marmoset EAE, where they appear directly responsible for the disintegration of myelin sheaths. Animals treated with control F(ab) fragments, i.e., directed against influenza antigen, revealed large demyelinating plaques in the cervical spinal cord, and animals treated with MOG-specific F(ab) fragments showed that the demyelinating activity of anti-MOG antibody in marmosets is dependent on intact Fc fragment function, as it can be competitively blocked in vivo by administration of MOG-specific F(ab) fragments.

Encephalitogenic Epitope Determination (MOG) in MS-like marmoset EAE. In C. jacchus marmosets with demyelinating EAE induced with recombinant rat MOG (rMOG: extracellular domain aa 1–125), the fine specificities of T-cell reactivity (proliferative responses in PBMC) and B-cell reactivity (serum antibody) to MOG were serially studied using overlapping 15-mer PIN-peptides (offsets of 1 and 3), corresponding to amino-acid sequences of both rat and human MOG (Chiron Mimotopes, San Diego, Calif.). Results: All animals studied (n=6) had a prominent and sustained T-cell response restricted to aa 27–36, a sequence totally conserved across species. A single marmoset responded to a second T-cell epitope located within aa 62–72. Serum antibody responses (n=10) mapped to 4 different regions of MOG including 2 major epitopes, aa 13–21 and aa 62–74 (100% and 60% of animals, respectively) and additional epitopes were identified in some animals (aa 28–36 and 40–45). No epitope spreading was observed either for T-cells or antibodies in animals with relapsing EAE that were monitored for up to 93 days. Conclusions: Encephalitogenic responses to MOG in MS-like, marmoset EAE appear restricted to a limited number of B-cell and T-cell epitopes. These findings demonstrate feasibility of specific immunotherapy in human MS.

Detecting B-cells with surface bound antibodies. B-cells were positively selected from freshly isolated peripheral blood mononuclear cells (PBMC) obtained from C. jacchus marmosets with MOG-induced EAE, from humans with MS and from healthy controls using anti-CD 19 coated beads. Slides containing $2 \times 10^5$ B-cells (>98% purity) were fixed with 1% glutaraldehyde and washed. The isolated B-cells were then incubated with labeled immunogold conjugates of a mixture of eleven 20-mer overlapping peptides corresponding to the sequence of the $NH_2$ terminus of human MOG (1–120); identical B-cell preparations were labeled with control polypeptides corresponding to the sequence of histone or MBP peptides. Slides were enhanced with silver and labeled B-cells were counted by two different blind observers.

B-cells expressing MOG-specific surface immunoglobulins were easily detected with the gold-conjugated MOG peptides in PBMC from MOG-immunized marmosets (n=8). In these animals which are known to develop serum anti-MOG antibodies, circulating MOG-specific B-cells occurred at a frequency of about 1:500 to about 1:2,000, increased from 0–1:10,000 in healthy, unimmunized marmosets (n=8). Unlabeled MOG peptides added in excess completely inhibited labeling and gold-conjugated control protein failed to label any B-cell. In humans, circulating MOG-specific B-cells could be detected in 8 of 17 MS patients (47%) and 9 of 18 healthy controls (50%). The frequency of these autoreactive B-cells ranged from about 1:11,000 to about 1:200,000 B-cells, with the highest frequencies observed in two patients with relapsing-remitting MS (1:16,000 and 1:11,000, respectively).

This immunogold assay sensitively detects MOG-specific B-cells in peripheral blood. This assay has a sensitivity of about 1:500, preferably of about 1:2,000, more preferably about 1:10,000, even more preferably about 1:15,000, and most preferably about 1:200,000. In humans, autoreactive B-cells can be detected in approximately 50% of individuals, and are equally present in MS patients and controls.

In the Examples above, MOG-specific antibodies were exclusively localized to areas where the transformation of compact myelin into small vesicles around single demyelinating axons occurred, and to myelin debris either floating in the CNS parenchyma or internalized by phagocytic cells (macrophages and microglia). Thus, in addition to a direct lytic attack on myelin and oligodendrocytes, these antibodies can also be responsible for receptor-mediated phagocytosis by macrophages, or antibody-dependent cellular cytotoxicity, which have long been recognized as possible effector mechanisms of myelin damage. Our experiments using passive transfer of antibody in the C. jacchus system have shown that it is possible to competitively block pathogenic effects of the monoclonal anti-MOG antibody 8.18.C5 by in vivo administration of recombinant F(ab) fragments, indicating that intact Fc fragments and not the MOG-specific CDR3 sequence themselves mediate the damage to myelin. Based on these findings, analogs or competitive inhibitors of antibody binding that are devoid of toxic effects on myelin provide a rational approach for therapy in EAE and related demyelinating disorders. Thus, the present invention utilizes compositions of autoantigen epitopes, anti-autoantigen antibody fragments or combinations thereof to effectuate treatment of demyelinating autoimmune diseases.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. Accordingly, it is intended that the scope of the present invention be limited solely by the scope of the following claims, including equivalents thereof.

What is claimed is:

1. An isolated polypeptide which specifically binds human myelin oligodendrocyte glycoprotein (MOG), said polypeptide comprising a pair of first and second antigen binding domain sequences, said pair selected from the group consisting of SEQ ID NOS:1 and 2, SEQ ID NOS:3 and 4, SEQ ID NOS:5 and 6, SEQ ID NOS:7 and 8, SEQ ID NOS:9 and 10, and SEQ ID NOS:11 and 12.

2. An isolated polypeptide according to claim 1, wherein the polypeptide is an F(ab).

3. A pharmaceutical composition comprising a polypeptide according to claim 1 and a pharmaceutically acceptable carrier.

4. A method of inhibiting MOG-antibody binding comprising the step of contacting a mixture of a MOG and an antibody with a polypeptide according to claim 1, whereby the MOG-antibody binding is inhibited.

5. A method of inhibiting MOG-antibody binding comprising the step of contacting a mixture of a MOG and an antibody with a polypeptide according to claim 2, whereby the MOG-antibody binding is inhibited.

6. A method of inhibiting demyelination associated with the binding of an autoantibody to a MOG polypeptide, comprising the step of administering to a marmoset or human host, subject to a pathogenic MOG polypeptide-polyclonal autoantibody binding, an effective amount of a composition comprising a polypeptide according to claim 1 not having a functional Fc portion and sufficient to specifically bind the MOG polypeptide and competitively inhibit the binding of the autoantibody to the MOG polypeptide, whereby the demyelination is inhibited.

7. A method of inhibiting demyelination associated with the binding of an autoantibody to a MOG polypeptide, comprising the step of administering to a marmoset or human host, subject to a pathogenic MOG polypeptide-polyclonal autoantibody binding, an effective amount of a composition comprising a polypeptide according to claim 2 not having a functional Fc portion and sufficient to specifically bind the MOG polypeptide and competitively inhibit the binding of the auto antibody to the MOG polypeptide, whereby the demyelination is inhibited.

8. A method of inhibiting demyelination associated withy the binding of an autoantibody to a MOG polypeptide, comprising the step of administering to a marmoset or human host, subject to a pathogenic MOG polypeptide-polyclonal autoantibody binding, an effective amount of a composition comprising a plurality of polypeptides according to claim 1 not having a functional Fc portion and sufficient to specifically bind the MOG polypeptide and competitively inhibit the binding of the autoantibody to the MOG polypeptide, whereby the demyelination is inhibited, wherein each of the plurality of polypeptides specifically binds a different MOG eptiope.

9. A method of inhibiting demyelination associated with the binding of an autoantibody to a MOG polypeptide, comprising the step of administering to a marmoset or human host, subject to a pathogenic MOG polypeptide-polyclonal autoantibody binding, an effective amount of a composition comprising a plurality of polypeptides according to claim 2 not having a functional Fc portion and sufficient to specifically bind the MOG polypeptide and competitively inhibit the binding of the autoantibody to the MOG polypeptide, whereby the demyelination is inhibited, wherein each of the plurality of polypeptides specifically binds a different MOG eptiope.

10. An isolated polypeptide according to claim 1, which specifically binds human myelin oligodendrocyte glycoprotein (MOG), said polypeptide comprising a pair of first and second antigen binding domain sequences, said pair being SEQ ID NOS:1 and 2.

11. An isolated polypeptide according to claim 1, which specifically binds human myelin oligodendrocyte glycoprotein (MOG), said polypeptide comprising a pair of first and second antigen binding domain sequences, said pair being SEQ ID NOS:3 and 4.

12. An isolated polypeptide according to claim 1, which specifically binds human myelin oligodendrocyte glycoprotein (MOG), said polypeptide comprising a pair of first and second antigen binding domain sequences, said pair being SEQ ID NOS:5 and 6.

13. An isolated polypeptide according to claim 1, which specifically binds human myelin oligodendrocyte glycoprotein (MOG), said polypeptide comprising a pair of first and second antigen binding domain sequences, said pair being SEQ ID NOS:7 and 8.

14. An isolated polypeptide according to claim 1, which specifically binds human myelin oligodendrocyte glycoprotein (MOG), said polypeptide comprising a pair of first and second antigen binding domain sequences, said pair being SEQ ID NOS:9 and 10.

15. An isolated polypeptide according to claim 1, which specifically binds human myelin oligodendrocyte glycoprotein (MOG), said polypeptide comprising a pair of first and second antigen binding domain sequences, said pair being SEQ ID NOS:11 and 12.

* * * * *

UNITED STATES PATENT AND TRADEMARK OFFICE
CERTIFICATE OF CORRECTION

PATENT NO. : 6,569,431 B2
DATED : May 27, 2003
INVENTOR(S) : von Büdingen et al.

It is certified that error appears in the above-identified patent and that said Letters Patent is hereby corrected as shown below:

Column 23,
Line 3, "auto antibody" should be -- autoantibody --;
Line 5, "withy" should be -- with --.

Signed and Sealed this

Fifteenth Day of July, 2003

JAMES E. ROGAN
*Director of the United States Patent and Trademark Office*